(12) United States Patent
Chakrabarti et al.

(10) Patent No.: US 9,181,251 B2
(45) Date of Patent: Nov. 10, 2015

(54) ANTI-MALARIAL COMPOUNDS FROM MARINE NATURAL PRODUCTS

(71) Applicants: Debopam Chakrabarti, Orlando, FL (US); Amy Wright, Ft. Pierce, FL (US)

(72) Inventors: Debopam Chakrabarti, Orlando, FL (US); Amy Wright, Ft. Pierce, FL (US)

(73) Assignees: University of Central Florida Research Foundation, Inc., Orlando, FL (US); Florida Atlantic University Board of Trustees, Ft. Pierce, FL (US)

( * ) Notice: Subject to any disclaimer, the term of this patent is extended or adjusted under 35 U.S.C. 154(b) by 0 days.

(21) Appl. No.: 14/104,569

(22) Filed: Dec. 12, 2013

(65) Prior Publication Data

US 2014/0200226 A1     Jul. 17, 2014

Related U.S. Application Data

(60) Provisional application No. 61/736,028, filed on Dec. 12, 2012.

(51) Int. Cl.

| | | |
|---|---|---|
| *A61K 31/497* | (2006.01) | |
| *A61K 31/4965* | (2006.01) | |
| *A61K 31/44* | (2006.01) | |
| *A61K 31/415* | (2006.01) | |
| *A61K 31/40* | (2006.01) | |
| *A61K 31/12* | (2006.01) | |
| *C07D 471/16* | (2006.01) | |
| *C07D 403/14* | (2006.01) | |
| *A61K 31/4178* | (2006.01) | |
| *C07C 50/02* | (2006.01) | |
| *A61K 31/122* | (2006.01) | |
| *A61K 31/4745* | (2006.01) | |
| *A61K 31/496* | (2006.01) | |
| *A61K 45/06* | (2006.01) | |
| *A61K 31/404* | (2006.01) | |

(52) U.S. Cl.
CPC ............ *C07D 471/16* (2013.01); *A61K 31/122* (2013.01); *A61K 31/404* (2013.01); *A61K 31/4178* (2013.01); *A61K 31/4745* (2013.01); *A61K 31/496* (2013.01); *A61K 31/497* (2013.01); *A61K 45/06* (2013.01); *C07C 50/02* (2013.01); *C07D 403/14* (2013.01)

(58) Field of Classification Search
CPC .............. A61K 31/122; A61K 31/404; A61K 31/4178; A61K 31/4745; A61K 31/496; A61K 31/497; A61K 45/06; C07C 50/02; C07D 403/14; C07D 471/16; C07K 5/06
USPC .............. 514/21.1, 254.09, 255.05, 280, 397, 514/414, 690; 540/460; 544/373, 405; 546/48; 548/312.1, 455; 568/375
See application file for complete search history.

(56) References Cited

U.S. PATENT DOCUMENTS

| | | | | |
|---|---|---|---|---|
| 4,970,226 | A | * | 11/1990 | Sun et al. ...................... 514/397 |
| 6,384,187 | B1 | * | 5/2002 | Wright et al. ................. 530/317 |

OTHER PUBLICATIONS

Bewley et al., "Microsclerodermins A and B. Antifungal Cyclic Peptides from the Lithistid Sponge Microscleroderma sp.", 1994, J. Am. Chem. Soc., vol. 116, No. 17, pp. 7631-7636.*

Alvarado, S., et al., "Novel anti-malarials from marine nature products", Presented at the Drug Discovery for Protozoan Parasites, Keystone Symposia, Breckenridge, Mar. 2009 and Molecular Parasitology Meeting, Woods Hole, Sep. 2009.

Roberts, B. et al., "Identification of Anti-malarial Activities form Marine Macroorganism Extracts", Keystone Symposium on "Drug Discovery of Protozoan Parasites", Santa Fe, NM, 2012.

Roberts, B. et al., "The Bis(Indolyl)Imidazole Alkaloid Nortopsentin A Exhibits Antiplasmodial Activity", Antimicrob Agents Chemother, May 2013, vol. 57(5), pp. 2362-2364.

* cited by examiner

*Primary Examiner* — My-Chau T Tran
(74) *Attorney, Agent, or Firm* — Timothy H. Van Dyke; Beusse, Wolter, Sanks & Maire, PLLC

(57) ABSTRACT

Novel compositions and methods for the treatment and prevention of malaria are disclosed herein.

12 Claims, 3 Drawing Sheets

NortopsentinA

ANTI-MALARIAL COMPOUNDS FROM MARINE NATURAL PRODUCTS

CROSS-REFERENCE TO RELATED APPLICATIONS

This application is related to U.S. Provisional Application No. 61/736,028 filed Dec. 12, 2012, to which priority is claimed under 35 USC 119. The disclosure of this provisional application is incorporated herein in its entirety by this reference.

STATEMENT OF GOVERNMENT RIGHTS

The invention with government support under Grant No. R21-AI-78376 awarded by the National Institutes of Health. Accordingly, the government has certain rights in the invention, as specified by law.

FIELD OF THE INVENTION

The present invention relates to novel anti-malarial compounds and methods for their use.

BACKGROUND OF THE INVENTION

Malaria is an infectious disease caused by a microorganism of the genus *Plasmodium*. Upon infection, the parasites (sporozoites) travel to the liver where they mature and release another form of parasites called merozoites. The parasites enter the bloodstream and multiply inside red blood cells, which then break open and infect more red blood cells. Malaria may be treated with oral medications such as chloroquine, quinine sulfate, hydroxychloroquine, mefloquine, atovaquone, and/or proguanil amongst other agents. It is known that these malarial parasites may evolve and become resistant to the administered medications. In many cases, the parasite is able to survive and continue to multiply despite being targeted with anti-malarial compounds.

BRIEF DESCRIPTION OF THE DRAWINGS

FIG. 1 shows exemplary Combiflash purification chromatograms for an active peak fraction, 10-V-00-3-003, from the genus *Aplysina*, which is a sponge found predominantly in the Atlantic Ocean.

FIG. 2 shows the structures of a number of compounds of several marine species with potent anti-malarial activities.

DETAILED DESCRIPTION OF THE INVENTION

Figure 1:
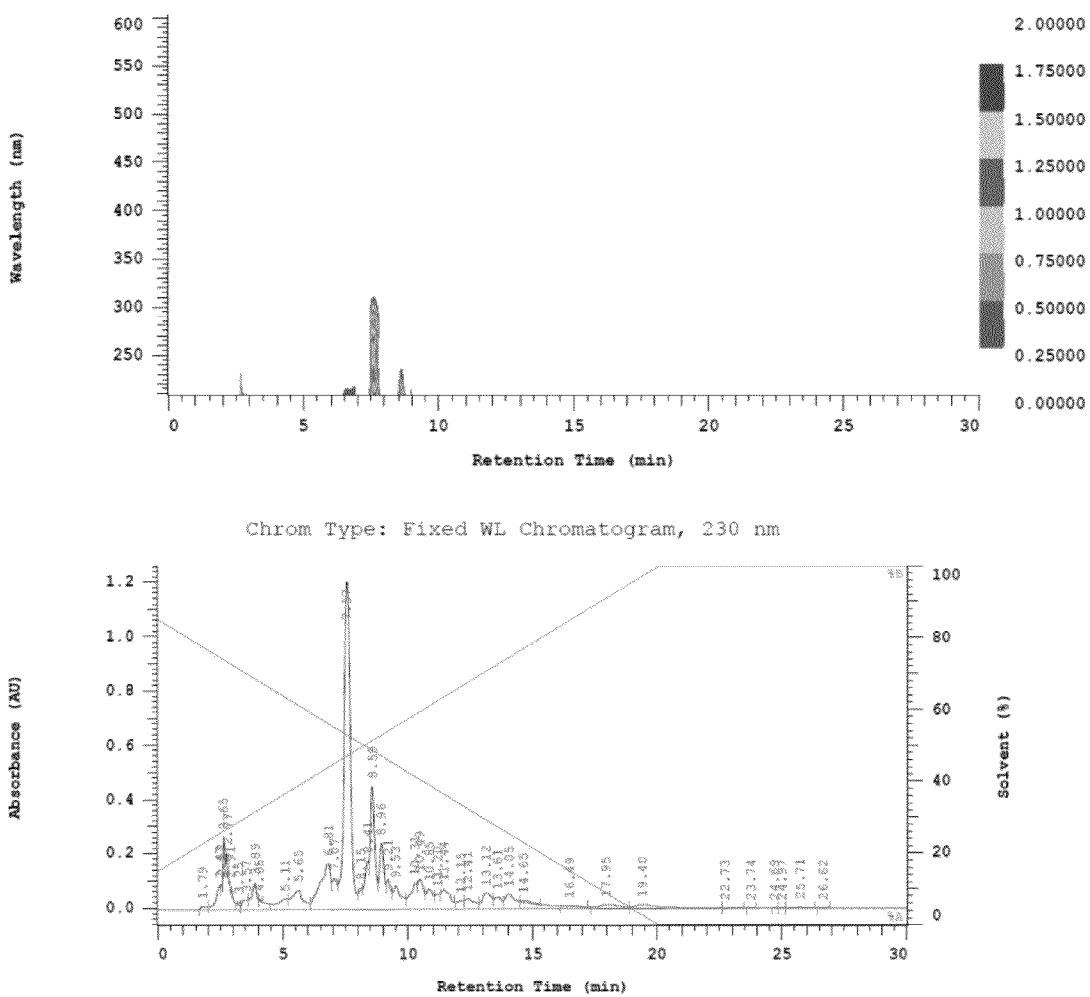
FIG. 1. Examples of Combiflash Chromatogram. Once fractions were isolated and found to be active against *P. falciparum* 3D7 strain of malaria, tested against the chloroquine-resistant Dd2 strain, and also tested for cyto-toxicity using the MTT cell viability assay, they were analyzed by LC-MS to identify the extracts with the greatest potential for novel chemistry leading to the identification of a number of leads that require further chemical investigation. Once the fractions were extracted and identified, they were dereplicated and purified using HPLC, Prep TLC and CCC.
Figure 1:
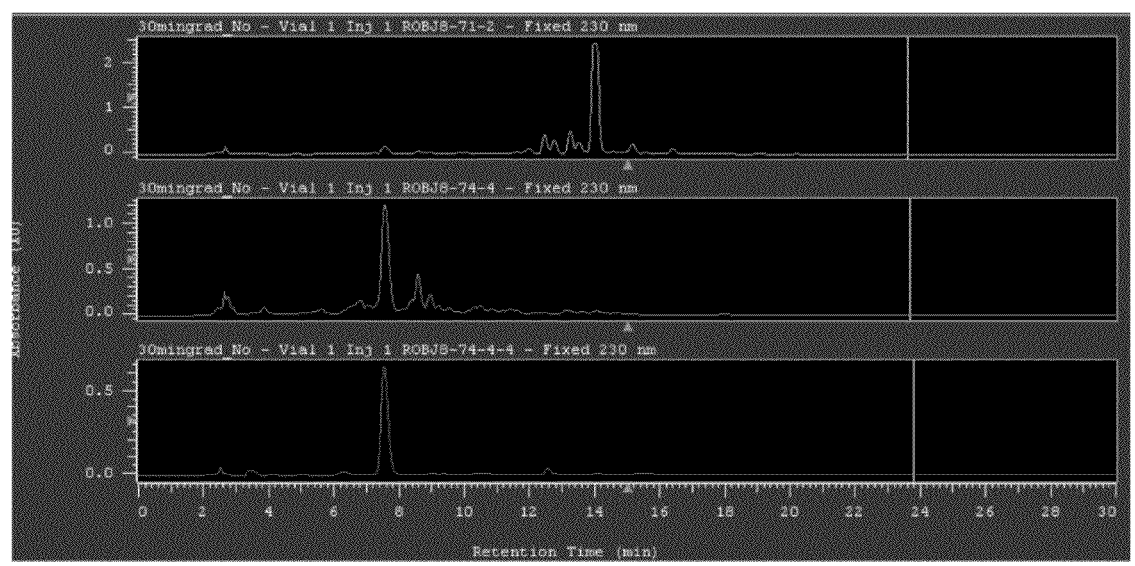

The present invention is directed to novel anti-malarial compounds that have been isolated from marine and natural products and have been found to have anti-malarial activity. These compounds have structures different from current anti-malarial compounds. Without wishing to be bound by theory, the novel compounds are thus expected to act upon novel cellular targets, which may alleviate the problem of drug resistance. The newly disclosed anti-malarial compounds include cembranoid-type diterpenes, microsclerodermins, dercitamides and bis-indoles. According to certain embodiments, the disclosure provides methods of treating or preventing malarial infection involving the administration of new anti-malarial agents taught herein to a subject in need.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. Prior to setting forth the invention in detail and for purposes of more clearly facilitating an understanding the invention as disclosed and claimed herein, the following definitions are provided.

As used herein, the terms "about" and "approximately" as used herein refers to—values that are ±10% of the stated value.

As used herein, the terms "administering" or "administration" of a composition as described herein to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the term "analog" refers to a compound having a structure similar to that of another one, but differing from it with respect to a certain component. The compound may differ in one or more atoms, functional groups, or substructures, which may be replaced with other atoms, groups, or substructures. In one aspect, such structures possess at least the same or a similar therapeutic efficacy.

As used herein, "anti-malarial" or "anti-malarial activity" includes any activity that decreases the infectivity, the reproduction, or inhibits the progress of the lifecycle of a malaria parasite. "Anti-malarial activity" includes inhibition of the growth of malaria infection by all of the means of observed with current anti-malarial drugs.

As used herein, the term "anti-malarial agent" refers to any compound having the formula designated by 2-12 as set forth herein, compounds shown in FIG. 2, compounds referred to in the Tables below, and any combinations, prodrugs, pharmaceutically acceptable salts, analogs, and derivatives thereof.

As used herein, "derivative" refers to a compound derived or obtained from another and containing essential elements of the parent compound. In one aspect, such a derivative possesses at least the same or similar therapeutic efficacy as the parent compound.

As used herein, by the term "effective amount" "amount effective," or the like, it is meant an amount effective at dosages and for periods of time necessary to achieve the desired result.

As used herein, the term "malaria" refers to an infectious disease spread by mosquitoes and caused by parasites of the genus *Plasmodium*.

As used herein, the term "parasite" refers to microorganisms that generally exploit the resources of its host body. Parasites may show a high degree of specialization and reproduce faster than their host. Parasites may also kill or reduce the biological mechanisms of the hosts.

As used herein, the term "pharmaceutically acceptable salt" is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citriccacid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As used herein, the term "preventing" means causing the clinical symptoms of the disease state not to worsen or develop, e.g., inhibiting the onset of disease, in a subject that may be exposed to or predisposed to the disease state, but does not yet experience or display symptoms of the full disease state, e.g., malaria.

As used herein, the term "prodrug" refers to a compound that is converted to a therapeutically active compound after administration, and the term should be interpreted as broadly herein as is generally understood in the art. Generally, but not necessarily, a prodrug is inactive or less active than the therapeutically active compound to which it is converted.

As used herein, the term "stereoisomer" refers to a compound which has the identical chemical constitution, but differs with regard to the arrangement of the atoms or groups in space.

As used herein, the term "subject" refers to any animal (e.g., a mammal), including, but not limited to, humans, which may be the recipient of a particular treatment.

As used herein, the terms "treating" or "treatment" or "alleviation" refers to both therapeutic treatment and prophylactic or preventative measures, wherein the objective is to prevent or slow down (lessen) the targeted pathologic condition or disorder.

Derivatives

According to certain embodiments, as used herein, derivatives of a compound (such as the anti-malarial agents set forth in FIG. 2) include salts, esters, enol ethers, enol esters, acetals, ketals, orthoesters, hemiacetals, hemiketals, solvates, hydrates, metabolites or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, alk(en)(yn)yl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, alk(en)(yn)yl, aryl, aralkyl, or cycloalkyl. Pharmaceutically acceptable enol esters include, but are not limited to, derivatives of formula C=C(OC(O)R) where R is hydrogen, alkyl, alkenyl, alkynyl, aryl, aralkyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

Figure 2:
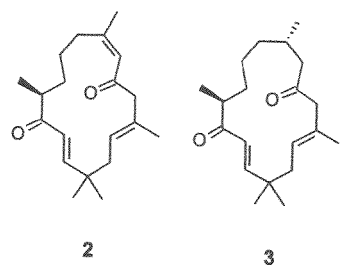
FIG. 2. Identification of a number of active compounds.
Figure 2:
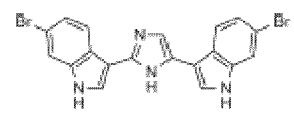
Figure 2:
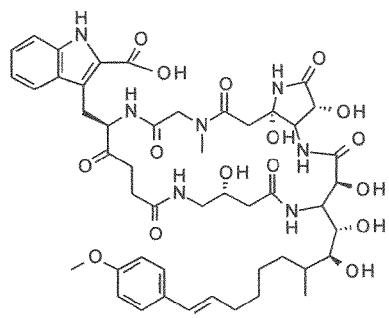
Figure 2:
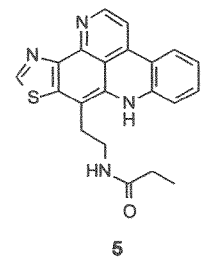
Figure 2:
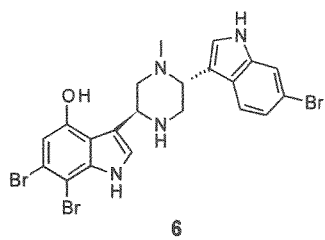
Figure 2:
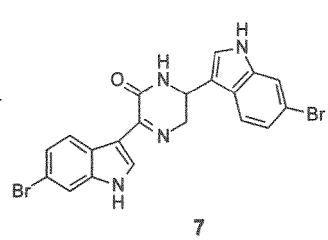
Figure 2:
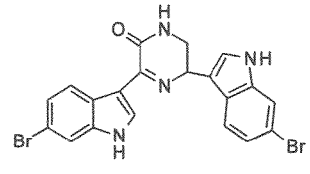
Figure 2:
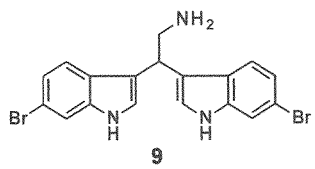
Figure 2:
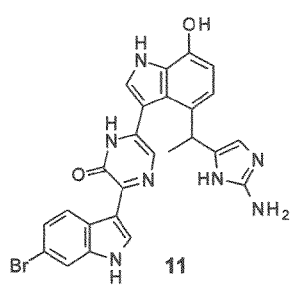
Figure 2:
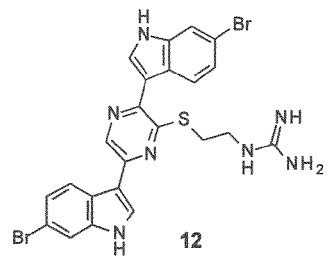
Figure 2:
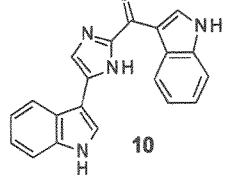

According to further embodiments, derivatives may include, but are not limited to, specific substitutions of reactive constituents on or emanating from a anti-malarial agent found in FIG. 2, and may include, but are not limited to, one or more of the following: a hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, thio, sulfhydryl, thioalkyl, alkylthio, sulfonyl, C1-C6 straight or branched chain alkyl, C2-C6 straight or branched chain alkenyl or alkynyl, aryl, aralkyl, heteroaryl, carbocycle, or heterocycle group or moiety, or $CO_2R_7$ where $R_7$ is hydrogen or C1-C9 straight or branched chain alkyl or C2-C9 straight or branched chain alkenyl group or moiety.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, alkyl refers to an unbranched or branched hydrocarbon chain. An alkyl group may be unsubstituted or substituted with one or more heteroatoms.

As used herein, alkenyl refers to an unbranched or branched hydrocarbon chain comprising one or more double bonds. The double bond of an alkenyl group may be unconjugated or conjugated to another unsaturated group. An alkenyl group may be unsubstituted or substituted with one or more heteroatoms.

As used herein, alkynyl refers to an unbranched or branched hydrocarbon chain comprising one of more triple bonds therein. The triple bond of an alkynyl group may be unconjugated or conjugated to another unsaturated group. An alkynyl group may be unsubstituted or substituted with one or more heteroatoms.

As used herein, alk(en)(yn)yl refers to an unbranched or branched hydrocarbon group comprising at least one double bond and at least one triple bond. The double bond or triple bond of an alk(en)(yn)yl group may be unconjugated or conjugated to another unsaturated group. An alk(en)(yn)yl group may be unsubstituted or substituted with one or more heteroatoms.

Exemplary alkyl, alkenyl, alkynyl, and alk(en)(yn)yl groups herein include, but are not limited to, methyl, ethyl, propyl, isopropyl, isobutyl, n-butyl, sec-butyl, tert-butyl, isopentyl, neopentyl, tert-pentyl, isohexyl, allyl(propenyl) and propargyl(propynyl).

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl or isoquinolinyl.

As used herein, "halo," "halogen," or "halide" refers to F, Cl, Br or I.

As used herein, base refers to any compound that accepts protons in water or solvent. Thus, exemplary bases include, but are not limited to, alkali metal hydroxides and alkali metal alkoxides (i.e., MOR, wherein M is an alkali metal such as but not limited to potassium, lithium, or sodium and R is hydrogen, alkyl, alkenyl, alkynyl, or alk(en)(yn)yl) such as but not limited to potassium hydroxide, potassium tert-butoxide, potassium tert-pentoxide, sodium hydroxide, sodium tert-butoxide, lithium hydroxide, etc.); other hydroxides such as but not limited to magnesium hydroxide (Mg(OH)2), calcium hydroxide (Ca(OH)2), or barium hydroxide (Ba(OH)2); alkali metal hydrides (i.e., MH, wherein M is as defined above) such as but not limited to sodium hydride, potassium hydride, or lithium hydride; carbonates such as but not limited to potassium carbonate (K2CO3), sodium carbonate (Na2CO3), potassium bicarbonate (KHCO3), or sodium bicarbonate (NaHCO3); alkyl ammonium hydroxides, alkenyl ammonium hydroxides, alkynyl ammonium hydroxides, or alk(en)(yn)yl ammonium hydroxides such as but not limited to n-tetrabutyl ammonium hydroxide (TBAH); amines such as ammonia, diethylamine, 2,2,6,6-tetramethyl piperidine (HTMP), tertiary amines (such as but not limited to dimethylethyl amine, diisopropylethylamine, trimethylamine, triethylamine, tributylamine, N-methylmorpholine, N-methylpyrrolidine, 1,8-diazabicyclo[5.4.0]-7-undecene (DBU), 1,5-diazabicyclo[4.3.0]-5-nonene (DBN), or tetramethylenediamine (TMEDA)), aromatic amines (such as but not limited to pyridine, collidine, lutidine, picoline, quinoline, or N,N-dimethylaniline); alkali metal amides such as but not limited to lithium amide, lithium dimethylamide, lithium diisopropylamide (LDA), lithium tetramethylpiperidide (LiTMP), or alkali metal hexamethyldisilazanes (such as but not limited to potassium hexamethyldisilazane, (KHMDS), sodium hexamethyldisilazane (NaH MDS), or lithium hexamethyldisilazane (LiHMDS)); alkyl lithiums, alkenyl lithiums, alkynyl lithiums, or alk(en)(yn)yl lithiums such as but not limited to n-butyl lithium sec-butyllithium, isopropyllithium; alkyl magnesium halides, alkenyl magnesium halides, alkynyl magnesium halides, or alk(en)(yn)yl magnesium halides such as but not limited to methyl magnesium bromide.

As used herein, solvent refers to any liquid that completely or partially dissolves a solid, liquid, or gaseous solute, resulting in a solution such as but not limited to hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone.

As used herein, dehydrating agent refers to any compound that promotes the formation of carboxamides from carboxylic acids, such as but not limited to thionyl chloride, sulfuryl chloride, a carbodiimide, an anhydride or a mixed anhydride, a phenol (such as but not limited to nitrophenol, pentafluorophenol, or phenol), or a compound of Formula (A):

wherein each of X and Y is independently an unsubstituted or substituted heteroaryl group (such as but not limited to imidazolyl, benzimidazolyl, or benzotriazolyl). Examples of dehydrating agents further include, but are not limited to, benzotriazole-1-yl-oxy-tris-(dimethylamino)-phosphonium hexafluorophosphate (BOP), N,N'-carbonyldiimidazole (CDI), 3-(diethoxyphosphoryloxy)-1,2,3-benzotriazin-4 (3H)-one (DEPBT), 1-ethyl-3-(3-dimethyllaminopropyl)carbodiimide (EDC), 2-(7-aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU), 1-hydroxybenzotriazole (HOBt), benzotriazole-1-yl-oxy-tris-pyrrolidino-phosphonium hexafluorophosphate (PyBOP), 2-(1H-benzotriazole-1-yl)-1,1,3,3-tetramethyluronium tetrafluoroborate (TBTU), O-(3,4-dihydro-4-oxo-1,2,3-benzotriazine-3-yl)-N,N,N,N-tetra methyluronium tetrafluoroborate (TDBTU), 3-(diethyloxyphosphoryloxy)-1,2,3-benzotriazin-4(3H)-one (DEPBT), dicyclohexylcarbodiimide (DCC), N,N'-diisopropylcarbodiimide (DIC), or 1-hydroxy-7-azabenzotriazole (HOAt). As used herein, acid refers to any compound that contains hydrogen and dissociates in water or solvent to produce positive hydrogen ions, as well as Lewis acids, including but not limited to hydrochloric acid, sulfuric acid, phosphoric acid, acetic acid, trihaloacetic acids (such as but not limited to trifluoroacetic acid or trichloroacetic acid), hydrogen bromide, maleic acid, sulfonic acids (such as but not limited to toluenesulfonic acids or camphorsulfonic acids), propionic acids (such as but not limited to (R)-chloropropionic acid), phthalamic acids (such as but not limited to N—[(R)-1-(1-naphthyl)ethyl]phthalamic acid), tartaric acids (such as but not limited to L-tartaric acid or dibenzyl-L-tartaric acid), lactic acids, camphoric acids, aspartic acids, or citronellic acids.

It is to be understood that reactants, compounds, solvents, acids, bases, catalysts, agents, reactive groups, or the like may be added individually, simultaneously, separately, and in any order. Furthermore, it is to be understood that reactants, compounds, acids, bases, catalysts, agents, reactive groups, or the like may be pre-dissolved in solution and added as a solution (including, but not limited to, aqueous solutions). In addition, it is to be understood that reactants, compounds, solvents, acids, bases, catalysts, agents, reactive groups, or the like may be in any molar ratio.

It is to be understood that reactants, compounds, solvents, acids, bases, catalysts, agents, reactive groups, or the like may be formed in situ.

Enantiomers/Tautomers

Anti-malarial agents of the disclosure also include where appropriate all enantiomers and tautomers of the agents, such as those disclosed in FIG. 2 and novel agents referred to herein. The man skilled in the art will recognize compounds that possess an optical properties (one or more chiral carbon atoms) or tautomeric characteristics. The corresponding enantiomers and/or tautomers may be isolated/prepared by methods known in the art.

Stereo and Geometric Isomers

Anti-malarial agents of the disclosure, such as those disclosed in FIG. 2 and novel agents referred to herein, may exist as stereoisomers and/or geometric isomers—e.g. they may possess one or more asymmetric and/or geometric centres and so may exist in two or more stereoisomeric and/or geometric forms. Contemplated herein is the use of all the individual stereoisomers and geometric isomers of those inhibitor agents, and mixtures thereof. The terms used in the claims encompass these forms, provided said forms retain the appropriate functional activity (though not necessarily to the same degree).

Anti-malarial agents of the disclosure also include all suitable isotopic variations of the agent or pharmaceutically acceptable salts thereof. An isotopic variation of an anti-malarial agent or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as 2H, 3H, 13C, 14C, 15N, 17O, 18O, 31P, 32P, 35S, 18F and 36Cl, respectively. Certain isotopic variations of the agent and pharmaceutically acceptable salts thereof, for example, those in which a radioactive isotope such as 3H or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Isotopic variations of the anti-malarial agents and pharmaceutically acceptable salts thereof of this disclosure can generally be prepared by conventional procedures using appropriate isotopic variations of suitable reagents.

Solvates

The anti-malarial agents of the disclosure, such as those disclosed in FIG. 2 and novel agents referred to herein, also include solvate forms of the agents. The terms used in the claims encompass these forms.

Polymorphs

The anti-malarial agents of the disclosure, such as those disclosed in FIG. 2 and novel agents referred to herein, also include their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

Embodiments of the disclosure further include anti-malarial agents, such as those disclosed in FIG. 2 and novel agents referred to herein, in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Metabolites

Also falling within the scope of this invention are the in vivo metabolic products of the anti-malarial agents, such as compounds of FIG. 2 described herein. A "metabolite" is a pharmacologically active product produced through metabolism in the body of a specified compound or salt thereof. Such products can result, for example, from the oxidation, reduction, hydrolysis, amidation, deamidation, esterification, deesterification, enzymatic cleavage, and the like, of the administered compound. Accordingly, the invention includes metabolites of compounds set forth in FIG. 2, including compounds produced by a process comprising contacting a compound of this invention with a mammal for a period of time sufficient to yield a metabolic product thereof.

Metabolites are identified, for example, by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

According to certain embodiments, provided are methods of preventing or treating malaria in a subject or preventing or treating a subject exhibiting a symptom of malaria. Malaria typically produces a string of recurrent attacks, or paroxysms, each of which has three stages—chills, followed by fever, and then sweating. Along with chills, the person is likely to have headache, malaise, fatigue, muscular pains, occasional nausea, vomiting, and diarrhea. Within an hour or two, the body temperature rises, and the skin feels hot and dry. Then, as the body temperature falls, a drenching sweat begins. The person, feeling tired and weak, is likely to fall asleep. A subject exhibiting one, two or more of the foregoing symptoms is considered a subject in need.

The following discussion will further describe the screening methods, compositions, and methods for treating and/or preventing malaria or a symptom of malaria as described herein.

1. Screening Methods

The present invention provides for screening marine natural products for new anti-malarial lead discovery compounds. In one aspect, fractions were confirmed as being active if the $IC_{50}$ was <5 µg/mL against the *P. falciparum* 3D7 strain using the SYBR Green I fluorescence-based assay. Fractions were derived from 20 different marine species. The top 35 fractions were then tested against the chloroquine-resistant Dd2 strain and were also tested for cyto-toxicity using the MTT cell viability assay. All fractions were then analyzed by LC-MS to identify active extracts with the greatest potential for novelty.

1.1. MNP Peak Fractions

MNP Peak Fractions were samples from the Harbor Branch Oceanographic Institute at Florida Atlantic University (HBOI) Peak Library. These fractions were extracted from 20 different marine species and potentially have anti-malarial activity against *P. falciparum* 3D7 strain and also were tested against chloroquine-resist and Dd2 strain.

1.2. Bioassay-Guided Fractionation

After active fractions were identified, they were dereplicated and purified using MPLC, HPLC, Prep TLC, and/or other column chromatography at the HBOI facility. FIG. 1 depicts an exemplary chromatogram from a purification conducted using the Isco Teledyne Combiflash™ instrument leading to an active peak fraction from the genus *Alpysina*, which is a sponge found predominantly in the Atlantic Ocean.

1.3 Aplysina

Active peak library fractions for *Aplysina* (HBOI Specimen Number 10-V-00-2033) were purified by HPLC and fractions submitted for assay. The most active of the peak library fractions contained two compounds that were difficult to separate. Originally, it was thought that a single compound was present in the fraction, but after additional and extensive HPLC method development, two compounds were successfully separated. This led to the identification of one of the active compounds from this faction as aeroplysinin-1.

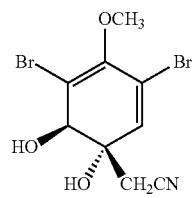

Aeroplysin-1 has been reported to have anti-malarial activity in the past (Gutierrez et. al. Pharmaceutical Biol. 2005, 43, 762-765).

1.4 *Bebryce* sp,

A peak library fraction fom this soft coarl (HBOI Specimen Number 10-V-00-1-004) showed activity in the primary screen. The soft coral was re-extracted with ethanol:ethyl acetate (9:1 v/v). The extract was partitioned between n-butanol and water and the n-butanol phase chromatographed using the Isco Combiflash system on a C-18 reverse phase column eluted with an acetonitrile-water gradient. HPLC of the active fraction using a Vydac C-18 column and isocratic mixtures of water:acetonitrile (45:55 v/v) led to the purification of a series of new cembranoid-type diterpenes as exemplified by compounds 2 and 3 of FIG. 2. Compound 3 (HB0141.001) gave an $IC_{50}$ of 2.5 uM (SI>64) against the *P. falciparum* Dd2 strain using the SYBR Green 1 fluorescence-based assay.

1.5 *Amphibleptula* sp.

A peak library fraction from this sponge (HBOI Specimen number 31-III-89-2-003) showed activity in the primary screen. The sponge was re-extracted with ethanol:ethyl acetate (9:1 v/v). The extract was partitioned first between ethyl acetate and water and then the aqueous phase was further partitioned with n-butanol. The n-butanol phase was chromatographed using the Isco Combiflash system on a C-18 reverse phase column eluted with an acetonitrile-water gradient. HPLC of the active fraction using a Vydac C-18 column and mixtures of water:acetonitrile led to the purification of microsclerodermin A, 4 (HBOI.41.C11) as the anti-malarial component of the fraction. The $IC_{50}$ of 4 was 0.73 uM (SI>58).

1.6 Choristida

A peak library fraction from this deep-water sponge (HBOI Specimen 23-XI-98-1-006) was active in the primary screen. Additional HPLC on this fraction using a C_18 column and mictures of acetonitrile in water containing 0.1% TFA led to a molecule (HB39.A10 IC50=2.3 uM SI>54) that provided very poor NMR spectra suggesting that it could be bound to a paramagnetic metal. Chelex purification to remove the metal resulted in the removal of the metal ion providing a compound with substantially better NMR spectra. 2D NMR and HRMS data suggested that the compound is dercitamide, 5. Dercitamide has been shown to have very moderate cytotoxicity and this is the first report of anti-malarial activity for this structure class. Provided in Table 1 below is data showing the inhibition activity of compounds 2-5 (shown in FIG. 2).

TABLE 1

| Compound | Dd2 $IC_{50}(\mu m)$ | Cytotoxicity $IC_{50}(\mu m)$ | Selectivity |
|---|---|---|---|
| Cembranoid-type diterpene (Compound 2) | 1.564 | 21.80 | 13.94 |
| Cembranoid-type diterpene (Compound 3) | 1.767 | 20.04 | 11.34 |
| Microsclerodermin A (Compound 4) | 0.075 | 3.53 | 47.07 |
| Dercitamide (Compound 5) | 1.051 | 14.85 | 14.13 |

Antiplasmodial activity was tested in *P falciparum* chloroquine resistant Dd2, and the cytotoxicity was assessed in NIH 3T3 fibroblasts cells. All 4 compounds showed a selectivity >10 with the compound 4 (microsclerodermin) exhibiting outstanding potency and selectivity

1.7 Bis-Indole Compounds as Anti-Malarial Agents

Based upon our earlier discovery of activity for nortopsentin A, a series of bis-indole compounds available from the HBOI Pure compound library, as well as peak library fractions from *Spongosorites* sp. that contained novel bis-indole metabolites were assayed. This identified additional compounds within the series with activity. The unusual *Spongosorites* (HBOI Specimen Number 21-V-93-3-001) led to the identification of a new bis-indole compound. Extraction of the sponge with ethanol followed by vacuum column chromatography using a step gradient of acetonitrile in water followed by a final column wash with acetonitrile:water:trifluoracetic acid 20:80:0.1 v/v/v led to the direct purification of compound 12. Its structure was identified using spectroscopic methods including NMR and MS. Earlier eluting fractions also show substantial activity but the active compounds have not yet been identified. A listing of activities for compounds labeled as 6-12 is set forth below in Table 2. The structures for compounds 6-12 can be found in FIG. 2. Compounds 6-12 are Dragmacidin, Hamacanthin A, Hamacanthin B, 2,2 bisindol-3-ylethyl amine, Deoxytopsentin, Dragmacidin D, and Dragmacidin G.

TABLE 2

| Compound | Tested As | P. falciparum IC$_{50}$ μm | NIH 3T3 IC$_{50}$ μm |
| --- | --- | --- | --- |
| Dragmacidin 6 | HBOI.43.BO5 | 6.4 | 7.8 |
| Hamacanthin A 7 | HBOI.43.BO6 | 3.2 | 30.4 |
| Hamacanthin B 8 | HBOI.43.BO7 | >20.6 | 38.6 |
| 2,2 bisindol-3-ylethyl amine 9 | HBOI.43.BO8 | 6.5 | 11.5 |
| Deoxytopsentin 10 | HBOI.43.BO4 | 8.4 | 20.2 |
| Dragmacidin D 11 | HBOI.43.BO3 | 5.2 | 27.7 |
| Dragmacidin G 12 | HBOI.43.BO2 | 6.4 | 7.8 |
| Nortopsentin A | (structure) | 0.6 | 6.0 |

Asynchronous cultures were exposed to different concentrations of inhibitor for 72 hrs. The IC$_{50}$ values were determined in the chloroquine-resistant Dd2 strain of the malarial parasite using SYBR Green-1 assays with Z-factors >0.9. The cytotoxicity against NIH 3T3 fibroblasts was evaluated using an MTS assay [(3-(4,5-dimethylthiazol-2-yl)-5-(3-carboxymethoxyphenyl)-2-(4-sulfophenyl)-2H-tetrazolium), CellTiter 96® Aqueous non-radioactive cell proliferation assay, Promega In a particular embodiment, a selectivity index, i.e., the ratio of a NIH 3T3 IC$_{50}$ value to a P. falciparum IC$_{50}$ value for the compound in a composition for treating or preventing malaria (or a symptom thereof) is about 10. As can be seen from Table 2, Hamacanthin A provides a desirable ratio of a NIH 3T3 IC$_{50}$ μm value to a P. falciparum IC$_{50}$ μm value of at least 9:1. Accordingly, in one embodiment, the composition comprises an amount of Hamacanthin A, and in a particular embodiment an effective amount of Hamacanthin A.

1.8 Results

All fractions that showed reproducible activity in the primary screen were analyzed by LCMS. The present inventors were successful in identifying compounds with anti-malarial activity from the HBOI Peak Library. The inventors had hypothesized that screening the HBOI peak library rather than crude extracts would lead to the rapid identification of active compounds and this was validated. In the majority of instances, crude extracts are submitted alongside the peak library fractions, and in nearly all instances, the crude extracts did not show activity in the screen-confirming the utility of screening enriched fractions. The dercitamide, microsclerodermin and bis-indole alkaloid classes of natural products have not previously been shown to have anti-malarial activity. The cembranoids from Bebryce sp. are unprecedented. The present inventors have successfully identified new structure classes, new lead fractions and future projects relevant to the discovery of anti-malarial agents.

1.9 Pharmaceutical Compositions

Aspects also provide pharmaceutical compositions comprising one or more anti-malarial agents that are identified by the screening methods provided herein or as are described herein. Anti-malarial agent(s) can be administered to a patient to achieve a therapeutic effect, e.g., active against parasites of malaria and in turn, treating and/or preventing malaria. Pharmaceutical compositions of the invention can comprise, for example, anti-malarial agents, compounds 2-12 as set forth above or their source fractions. In certain embodiments, the active agents were identified by a screening method embodiment described herein, which were identified by their activity against P. falciparum 3D7. The compositions can be administered alone or in combination with at least one other agent, such as a stabilizing compound, which can be administered in any sterile, biocompatible pharmaceutical carrier, including, but not limited to, saline, buffered saline, dextrose, and water. The compositions can be administered to a subject alone, or in combination with other therapeutic agents or treatments as described below.

In addition to the active ingredients, these pharmaceutical compositions can contain suitable pharmaceutically acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

1.10 Determination of a Therapeutically Effective Dose

The determination of a therapeutically effective dose of therapeutic agents identified by a screening method herein is well within the capability of those skilled in the art. A therapeutically effective dose refers to that amount of active ingredient which shows activity against malarial parasites. One example is if activities of IC$_{50}$ of <10 μg/ml against P. falciparum 3D7 using malaria parasite growth inhibition assays. Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Preferably, a therapeutic agent gains access to the parasite or the infected red blood cell for the duration of time necessary for its normal action.

1.11 Symptoms

The compounds and compositions as described herein may be utilized for the treatment or prevention of one or more symptoms of malaria. The signs and symptoms of malaria often begin 8-25 days following infection, but may occur later in those who have taken anti-malarial medications as prevention. Symptoms may include but are not limited to fever, shivering, arthralgia (joint pain), vomiting, hemolytic anemia, jaundice, hemoglobinuria, retinal damage, e.g., retinal whitening, abnormal posture, and convulsions. The classic symptoms of malaria include the cyclical occurrence of sudden coldness, rigor, fever and sweating lasting about two hours or more, occurring every 2-4 days. In some cases, the fever may be continuous. Severe symptoms, which are more likely in the case of *P. falciparum* infection, include splenomegaly (enlarged spleen), severe headache, cerebral ischemia, hepatomegaly (enlarged liver), hypoglycemia, and hemoglobinuria with renal failure.

1.12 Conjunctive Therapeutic Agents

In any of the embodiments described above, any of the compounds and/or compositions of the invention can be co-administered with other appropriate therapeutic agents (conjunctive agent or conjunctive therapeutic agent) or therapies for the treatment or prevention of malaria and/or a symptom thereof. Selection of the appropriate conjunctive agents or therapies for use in combination therapy can be made by one of ordinary skill in the art, according to conventional pharmaceutical principles. The combination of therapeutic agents or therapies can act synergistically to effect the treatment or prevention of malaria or a symptom thereof. Using this approach, one may be able to achieve therapeutic efficacy with lower dosages of each agent, thus reducing the potential for adverse side effects.

Exemplary conjunctive agents that may be formulated and/or administered with a compound as described herein include, but are not limited to chloroquine (Aralen), quinine, tetracycline, clindamycin (Cleocin), mefloquin (Lariam), sulfadoxone/pyrimethamine (Fansidar), primaquine and halofantrine. It is appreciated that suitable conjuvant therapeutic agents for use in the present invention may also comprise any combinations, prodrugs, pharmaceutically acceptable salts, analogs, and derivatives thereof.

The mode of administration for a conjunctive formulation in accordance with the present invention is not particularly limited, provided that the one or more of compounds 2-12 ("novel anti-malarial agents") as described herein and the conjunctive agent are combined upon administration. Such an administration mode may, for example, be (1) an administration of a single formulation obtained by formulating a novel anti-malarial agent and a conjunctive agent simultaneously; (2) a simultaneous administration via an identical route of the two agents obtained by formulating a novel anti-malarial agent and a conjunctive agent separately; (3) a sequential and intermittent administration via an identical route of the two agents obtained by formulating a novel anti-malarial agent and a conjunctive agent separately; (4) a simultaneous administration via different routes of two formulations obtained by formulating a novel anti-malarial agent and a conjunctive agent separately; and/or (5) a sequential and intermittent administration via different routes of two formulations obtained by formulating a novel anti-malarial agent and a conjunctive agent separately (for example, a novel anti-malarial agent followed by a conjunctive agent, or inverse order) and the like.

The dose of a conjunctive formulation may vary depending on the formulation of the novel anti-malarial agent and/or the conjunctive agent, the subject's age, body weight, condition, and the dosage form as well as administration mode and duration. One skilled in the art would readily appreciate that the dose may vary depending on various factors as described above, and a less amount may sometimes be sufficient and an excessive amount should sometimes be required.

The conjunctive agent may be employed in any amount within the range causing no problematic side effects. The daily dose of a conjunctive agent is not limited particularly and may vary depending on the severity of the disease, the subject's age, sex, body weight and susceptibility as well as time and interval of the administration and the characteristics, preparation, type and active ingredient of the pharmaceutical formulation. An exemplary daily oral dose per kg body weight in a subject, e.g., a mammal, is about 0.001 to 2000 mg, preferably about 0.01 to 500 mg, more preferably about 0.1 to about 100 mg as medicaments, which is given usually in 1 to 4 portions.

When the novel anti-malarial agent and a conjunctive agent are administered to a subject, the agents may be administered at the same time, but it is also possible that a conjunctive agent is first administered and then a novel anti-malarial agent is administered, or that a novel anti-malarial agent is first administered and then a conjunctive agent is administered. When such an intermittent administration is employed, the time interval may vary depending on the active ingredient administered, the dosage form and the administration mode, and for example, when a conjunctive agent is first administered, a novel anti-malarial agent may be administered within 1 minute to 3 days, preferably 10 minutes to 1 day, more preferably 15 minutes to 1 hour after the administration of the conjunctive agent. When a novel anti-malarial agent is first administered, for example, then a conjunctive agent may be administered within 1 minute to 1 day, preferably 10 minutes to 6 hours, more preferably 15 minutes to 1 hour after the administration of a novel anti-malarial agent.

It is understood that when referring to a novel anti-malarial agent and a conjunctive agent, it is meant a novel anti-malarial agent alone, a conjunctive agent alone, as a part of a composition, e.g., composition, which optionally includes one or more pharmaceutical carriers. It is also contemplated that more than one conjunctive agent may be administered to the subject if desired.

1.13 References

All references set forth herein in this document are incorporated by reference herein to the extent that the subject matter therein does not conflict with the existing disclosure.

1. Roberts, B., S. Alvarado, A. Wright, and D. Chakrabarti. *Antimicrob Agents Chemother.* 2013 57(5)2362-2364.

It should be borne in mind that all patents, patent applications, patent publications, technical publications, scientific publications, and other references referenced herein and in the accompanying appendices are hereby incorporated by reference in this application to the extent not inconsistent with the teachings herein.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A method for treating malaria in a subject comprising administering to a subject in need thereof an effective amount of a composition comprising a compound having one of the following structures:

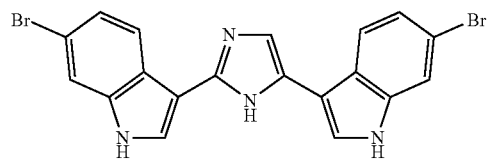

Nortopsentin A

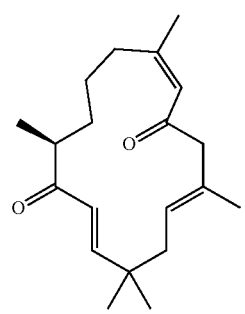

2

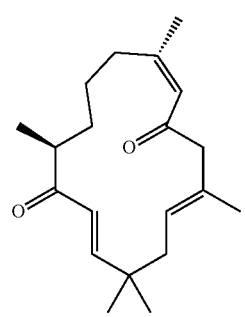

3

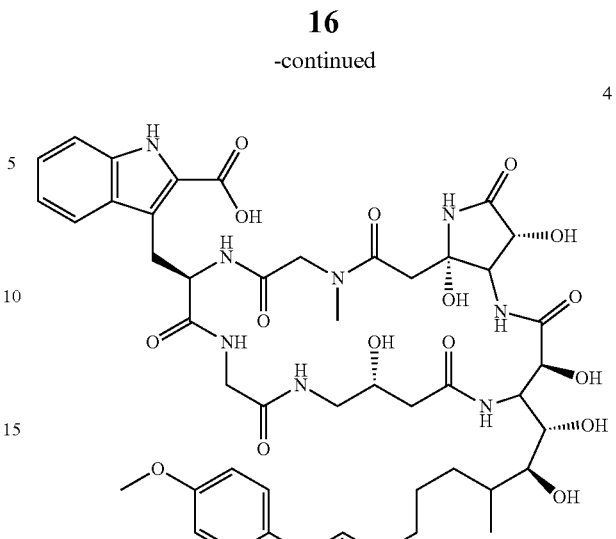

4

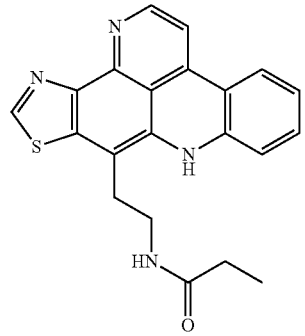

5

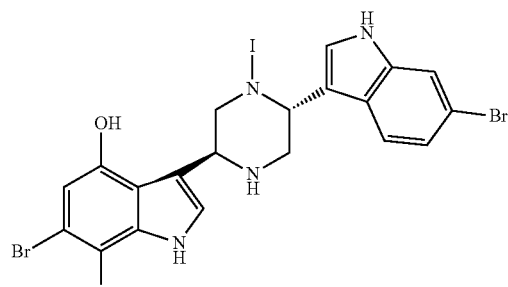

6

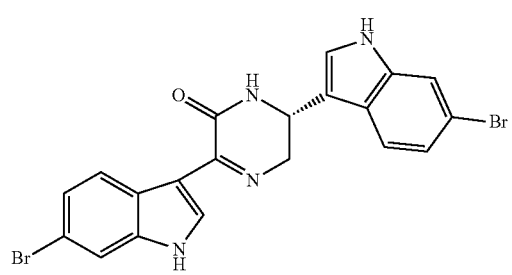

7

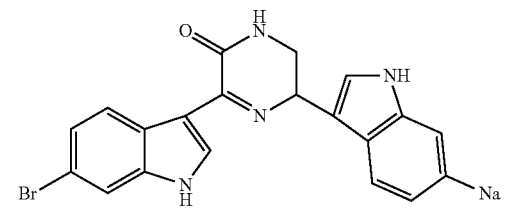

8

-continued

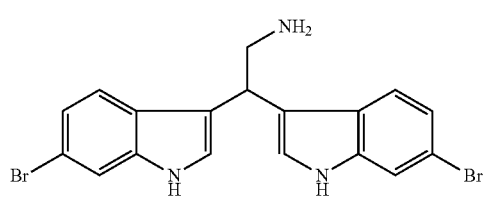
9

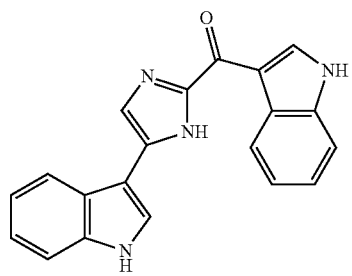
10

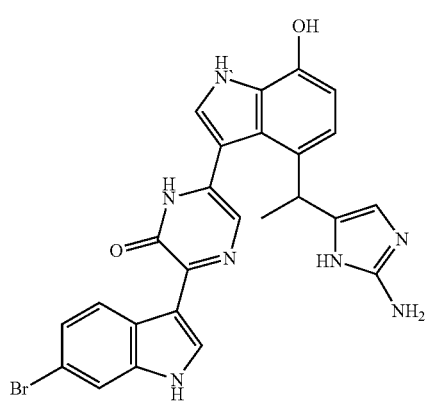
11

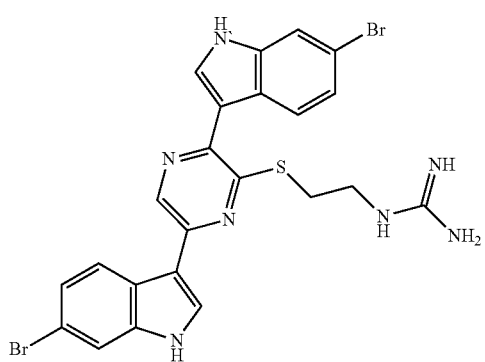
12

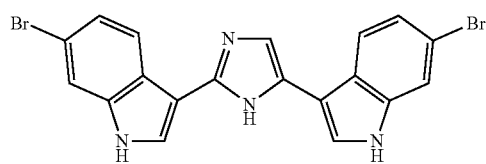
Nortopsentin A

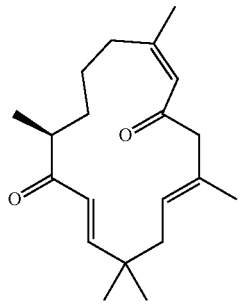
2

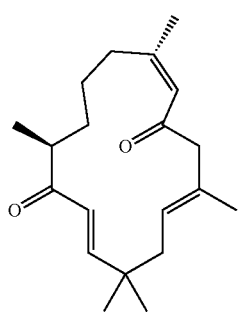
3

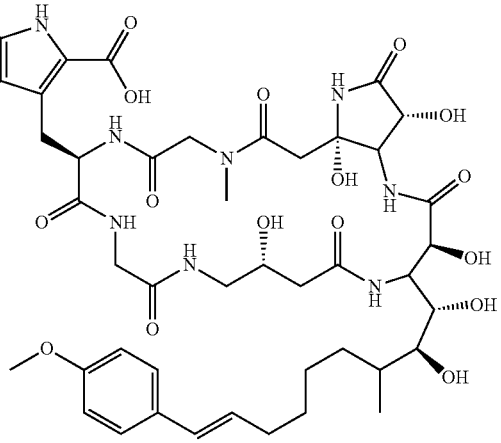
4

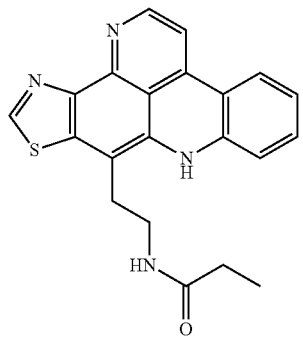
5 or is an analog, combination, derivative, prodrug, stereoisomer, or pharmaceutically acceptable salt thereof.

2. The method of claim 1, wherein composition further comprises a pharmaceutically acceptable carrier.

3. The method of claim 1, further comprising administering a conjunctive anti-malarial agent to the subject.

4. The method of claim 1, wherein the compound of the composition comprises a ratio of a NIH 3T3 $IC_{50}$ μm value to a *P. falciparum* $IC_{50}$ μm value of at least 9:1.

5. A method for treating a condition in a subject in need, the method comprising administering to the subject an effective amount of a composition, wherein the condition comprises of a symptom of malaria; wherein the composition comprises a compound having one of the following structures:

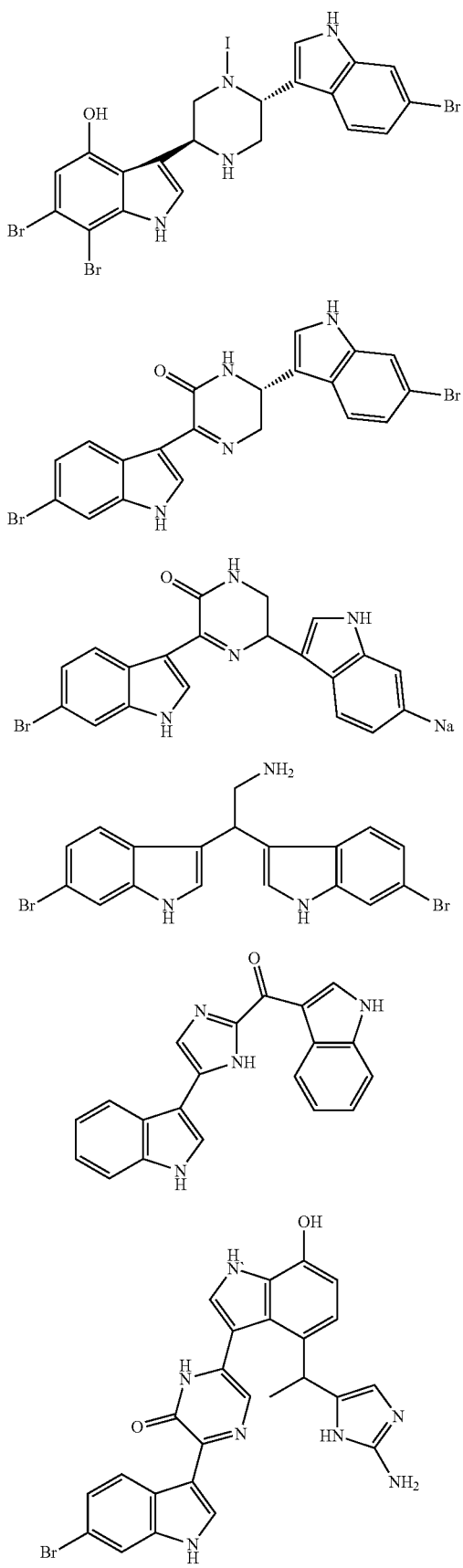

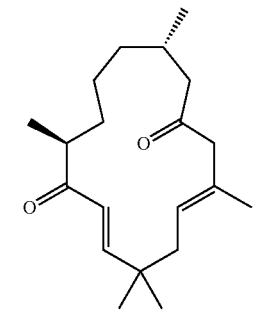

or is an analog, combination, derivative, prodrug, stereoisomer, or pharmaceutically acceptable salt thereof.

6. The method of claim 5, wherein composition further comprises a pharmaceutically acceptable carrier.

7. The method of claim 5, further comprising administering a conjunctive anti-malarial agent to the subject.

8. The method of claim 5, wherein the composition comprises a compound with the following structure:

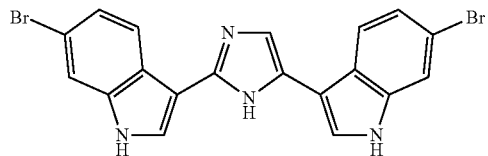

or is an analog, derivative, prodrug, stereoisomer, or pharmaceutically acceptable salt thereof.

9. A method of treating malaria by killing or arresting the growth of *F. Plasmodium* in a subject in need thereof, the method comprising administering to the subject an effective amount of a composition comprising a compound having one of the following structures:

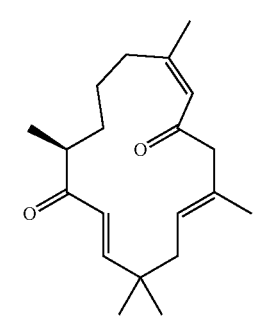

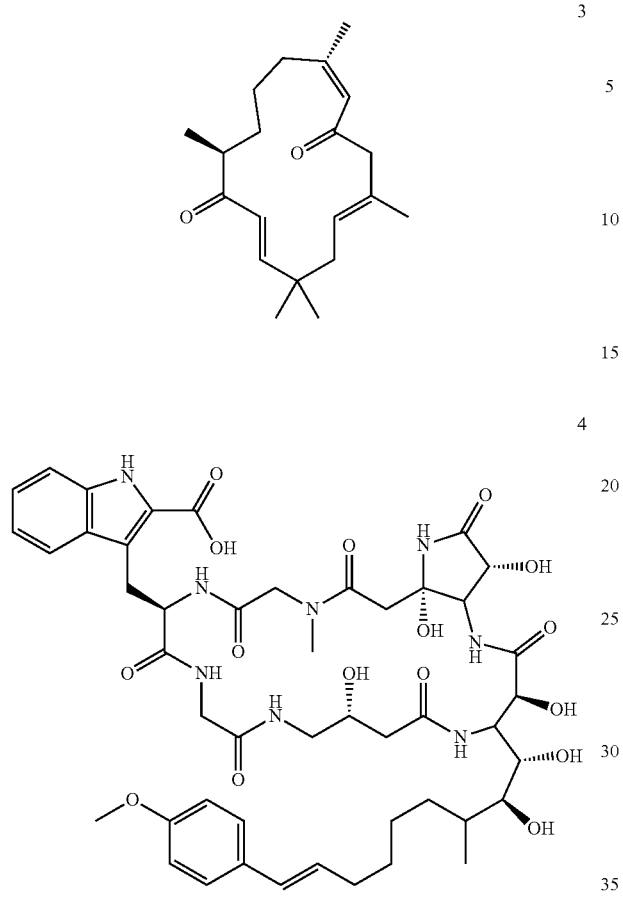
3
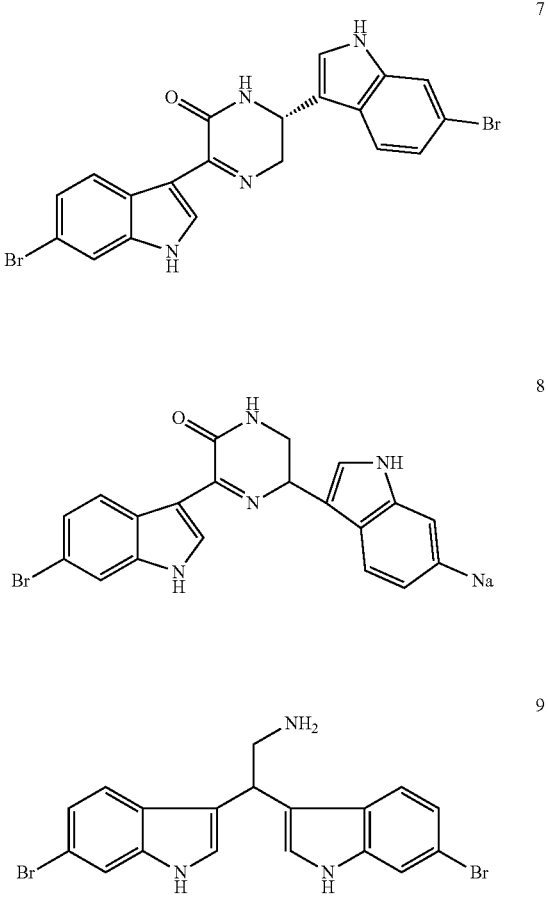
4
5
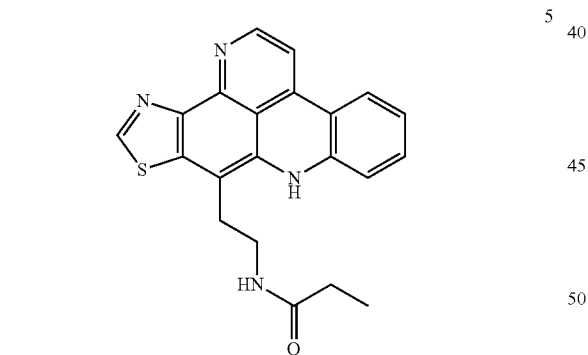
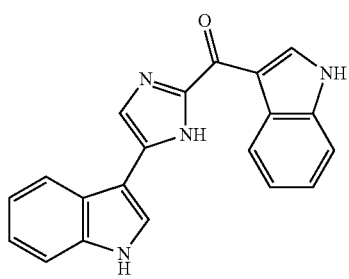
7
8
9
6
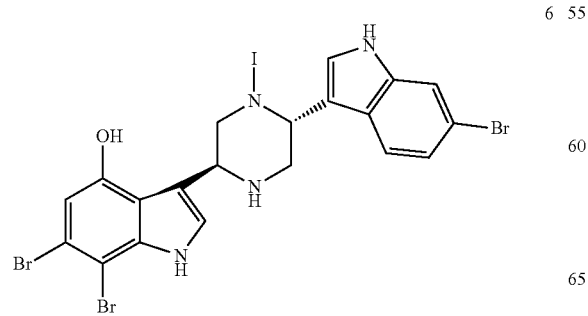
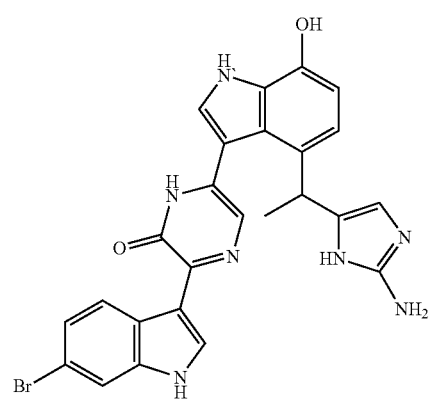
10
11

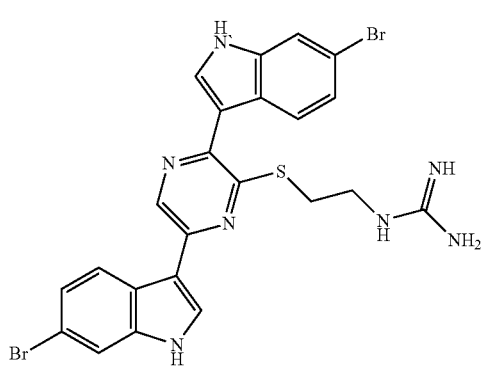

or is an analog, combination, derivative, prodrug, stereoisomer, or pharmaceutically acceptable salt thereof.

10. The method of claim 9, wherein composition further comprises a pharmaceutically acceptable carrier.

11. The method of claim 9, further comprising administering a conjunctive anti-malarial agent to the subject.

12. The method of claim 9, wherein the composition comprises a compound the following structure:

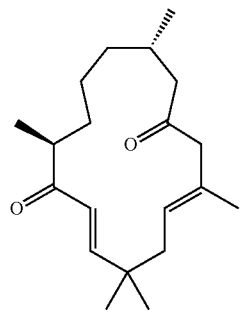

or is an analog, derivative, prodrug, stereoisomer, or pharmaceutically acceptable salt thereof.

* * * * *